(12) United States Patent
Johnson

(10) Patent No.: US 7,915,488 B2
(45) Date of Patent: Mar. 29, 2011

(54) PUMPKIN LINE HWN 130-1018T

(75) Inventor: William C. Johnson, Sacramento, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 12/197,808

(22) Filed: Aug. 25, 2008

(65) Prior Publication Data

US 2009/0064362 A1 Mar. 5, 2009

Related U.S. Application Data

(60) Provisional application No. 60/968,869, filed on Aug. 29, 2007.

(51) Int. Cl.
*A01H 5/00* (2006.01)
*A01H 5/10* (2006.01)
*A01H 1/00* (2006.01)
*C12N 15/82* (2006.01)
*C12Q 1/68* (2006.01)
*A01D 46/00* (2006.01)

(52) U.S. Cl. ............ 800/310; 800/260; 800/278; 435/6; 47/1.01 R

(58) Field of Classification Search .................... 800/310
See application file for complete search history.

(56) References Cited

U.S. PATENT DOCUMENTS

| 5,677,157 | A | 10/1997 | Chee ............................ 435/172.3 |
| 5,998,699 | A | 12/1999 | Slightom et al. ............... 800/205 |
| 6,337,431 | B1 * | 1/2002 | Tricoli et al. .................. 800/280 |
| 7,166,772 | B2 * | 1/2007 | Superak ......................... 800/310 |

OTHER PUBLICATIONS

Whitaker et al 1986, Squash Breeding, In Breeding Vegetable Crops, Bassett, ed. Avi Publishing Co. Inc, Westport, CT, pp. 209-242.*
U.S. Appl. No. 12/197,812, filed Aug. 25, 2008, Johnson.
"Availability of Determination of nonregulated status for virus resistant squash," Animal and Plant Health Inspection Service, USDA, Federal Register, 59(238):64187-64189, Dec. 13, 1994.

* cited by examiner

*Primary Examiner* — Anne Kubelik
(74) *Attorney, Agent, or Firm* — Alissa Eagle, Esq.; SNR Denton US LLP

(57) ABSTRACT

The invention provides seed and plants of the pumpkin line designated HWN 130-1018T. The invention thus relates to the plants, seeds and tissue cultures of pumpkin line HWN 130-1018T, and to methods for producing a pumpkin plant produced by crossing a plant of pumpkin line HWN 130-1018T with itself or with another pumpkin plant, such as a plant of another line. The invention further relates to seeds and plants produced by such crossing. The invention further relates to parts of a plant of pumpkin line HWN 130-1018T, including the fruit and gametes of such plants.

24 Claims, No Drawings

PUMPKIN LINE HWN 130-1018T

This application claims the priority of U.S. Provisional Appl. Ser. No. 60/968,869, filed Aug. 29, 2007, the entire disclosure of which is incorporated herein by reference.

BACKGROUND OF THE INVENTION

1. Field of the Invention

The present invention relates to the field of plant breeding and, more specifically, to the development of *Cucurbita pepo* Halloween type pumpkin line HWN 130-1018T.

2. Description of Related Art

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is the pumpkin. Pumpkin is one common name for members of the genus *Cucurbita* of the family Cucurbitaceae which are harvested as fully mature fruits. *Cucurbita* species include *Cucurbita pepo, Cucurbita maxima, Cucurbita mixta*, and *Cucurbita moschata*. In the United States, the thick-growing, small-fruited bush, or non-trailing varieties of *C. pepo* grown for immature fruit harvest are called summer squash or zucchini, and the long-season, long-trailing, large-fruited varieties are called pumpkin or winter squashes. Certain types of fruits often referred to as pumpkin are also found in *C. moshata, C. maxima*, and *C. mixta*. Regardless of species, "pumpkin" usually refers to the fruit of the genus *Cucurbita*. Halloween type pumpkins (exclusively *Cucurbita pepo*) can be used as a table vegetable or in pies, but are used most commonly used exclusively for autumn decoration. White, red, and gray varieties of pumpkin fruit are also available. Additionally, pumpkin seeds, either hulled or hull-less, can be roasted and consumed. Pumpkin seeds are a good source of iron and minerals.

Botanically, the fleshy, edible portion of the pumpkin is a fruit, but is conventionally considered a vegetable. The pumpkin fruit may be very large or small, but are typically grown to the mature stage. Pumpkins that are grown to maturity for use as Jack-o-lanterns or as pie ingredients often have a stringy coarse flesh that varies in color from orange to yellow to white. The stems of the genus *Cucurbita* usually help identify the species. For example, *C. pepo* and *C. mixta* have hard, five-angled stems, but *C. moschata* has a long, slender, columnar five-angled stem, and *C. maxima* has a soft, round stem. The leaves of *Cucurbita* are simple with 3-5 lobes.

*Cucurbita* plants generally have bright yellow monoecious flowers. Like stem morphology, peduncle morphology may help identify the different species. *C. pepo* typically have a 5-8 ridged peduncle with deep grooves; *C. maxima* typically have a cylindrical peduncle without any grooves; *C. moschata* and *C. mixta* typically have five-ridged peduncles that flare at the fruit attachment point, but the *C. mixta* peduncle is typically rounded and only slightly flared. All *Cucurbita* spp. typically have separate male and female flowers, requiring a pollinizer to enable fruit and seed development. Cross-pollination is possible between some pairs of the different *Cucurbita* species, though may be very difficult. *Cucurbita* spp. have spiny, sticky pollen that requires active pollinators. In the past, most pumpkins were pollinated by squash bees, but now most commercially grown pumpkins are pollinated by honeybees or hand pollinated.

*C. pepo* is a diploid species, with 2n=24 chromosomes. Most commercially grown pumpkins are F1 hybrids. Representative varieties include "Baby Boo" (white) and "Munchkin" which are both miniature *C. pepo;* "Prizewinner," and "Big Moon," which are both jumbo *C. maxima;* and "Magic Lantern," "Jackpot," "Autumn Gold," and "Frosty." "Small Sugar" and "Winter Luxury" are both representative cooking varieties of pumpkin.

Pumpkin is cultivated worldwide, though the Halloween type pumpkin is grown widely only in the U.S. and parts of Canada. In the U.S., the principal pumpkin growing states include Illinois, Ohio, California, Michigan, Pennsylvania, New York, and Texas, though they are produced in every state. Most pumpkin is direct seeded in tilled fields, but transplants are also used. No-till production is possible, but may be complicated by weed and disease problems. Fertilizer application to the beds is often required, and preferably is complete before planting. Pumpkin is a warm season crop that typically matures in 70-115 days depending on variety and environment; giant pumpkins and some tropically adapted pumpkins may require 150 days or more to mature.

While breeding efforts to date have provided a number of useful pumpkin lines with beneficial traits, there remains a great need in the art for new lines with further improved traits. Such plants would benefit farmers and consumers alike by improving crop yields and/or quality.

SUMMARY OF THE INVENTION

In one aspect, the present invention provides a pumpkin plant of the line designated HWN 130-1018T. Also provided are pumpkin plants having all the physiological and morphological characteristics of the pumpkin line designated HWN 130-1018T. Parts of the pumpkin plant of the present invention are also provided, for example, including pollen, an ovule, scion, a rootstock, a fruit, and a cell of the plant.

The invention also concerns the seed of pumpkin line HWN 130-1018T. The pumpkin seed of the invention may be provided as an essentially homogeneous population of pumpkin seed of the line designated HWN 130-1018T. Essentially homogeneous populations of seed are generally free from substantial numbers of other seed. Therefore, seed of line HWN 130-1018T may be defined as forming at least about 97% of the total seed, including at least about 98%, 99% or more of the seed. The population of pumpkin seed may be particularly defined as being essentially free from hybrid seed. The seed population may be separately grown to provide an essentially homogeneous population of pumpkin plants designated HWN 130-1018T.

In another aspect of the invention, a plant of pumpkin line HWN 130-1018T comprising an added heritable trait is provided. The heritable trait may comprise a genetic locus that is, for example, a dominant or recessive allele. In one embodiment of the invention, a plant of pumpkin line HWN 130-1018T is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a pumpkin plant of line HWN 130-1018T is provided. The tissue culture will preferably be capable of regenerating pumpkin plants capable of expressing all of the physiological and morphological characteristics of the line, and of regenerating plants having substantially the same genotype as other plants of the line. Examples of some of the physiological and morphological characteristics of the line HWN 130-1018T include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides pumpkin plants regenerated from a tissue culture of the invention, the plants having all the physiological and morphological characteristics of line HWN 130-1018T.

In yet another aspect of the invention, processes are provided for producing pumpkin seeds, plants and fruit, which processes generally comprise crossing a first parent pumpkin plant with a second parent pumpkin plant, wherein at least one of the first or second parent pumpkin plants is a plant of the line designated HWN 130-1018T. These processes may be further exemplified as processes for preparing hybrid pumpkin seed or plants, wherein a first pumpkin plant is crossed with a second pumpkin plant of a different, distinct line to provide a hybrid that has, as one of its parents, the pumpkin plant line HWN 130-1018T. In these processes, crossing will result in the production of seed. The seed production occurs regardless of whether the seed is collected or not.

In one embodiment of the invention, the first step in "crossing" comprises planting seeds of a first and second parent pumpkin plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent pumpkin plants into plants that bear flowers. A third step may comprise preventing self-pollination of the plants, such as by emasculating the male portions of flowers, (i.e., treating or manipulating the flowers to produce an emasculated parent pumpkin plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent pumpkin plants. Yet another step comprises harvesting the seeds from at least one of the parent pumpkin plants. The harvested seed can be grown to produce a pumpkin plant or hybrid pumpkin plant.

The present invention also provides the pumpkin seeds and plants produced by a process that comprises crossing a first parent pumpkin plant with a second parent pumpkin plant, wherein at least one of the first or second parent pumpkin plants is a plant of the line designated HWN 130-1018T. In one embodiment of the invention, pumpkin seed and plants produced by the process are first generation ($F_1$) hybrid pumpkin seed and plants produced by crossing a plant in accordance with the invention with another, distinct plant. The present invention further contemplates plant parts of such an $F_1$ hybrid pumpkin plant, and methods of use thereof. Therefore, certain exemplary embodiments of the invention provide an F1 hybrid pumpkin plant and seed thereof.

In still yet another aspect, the present invention provides a method of producing a plant derived from line HWN 130-1018T, the method comprising the steps of: (a) preparing a progeny plant derived from line HWN 130-1018T, wherein said preparing comprises crossing a plant of the line HWN 130-1018T with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line HWN 130-1018T. The plant derived from line HWN 130-1018T may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line HWN 130-1018T is obtained which possesses some of the desirable traits of the line as well as potentially other selected traits.

In certain embodiments, the present invention provides a method of producing pumpkins comprising: (a) obtaining a plant of pumpkin line HWN 130-1018T, wherein the plant has been cultivated to maturity, and (b) collecting pumpkins from the plant.

In still yet another aspect of the invention, the genetic complement of the pumpkin plant line designated HWN 130-1018T is provided. The phrase "genetic complement" is used to refer to the aggregate of nucleotide sequences, the expression of which sequences defines the phenotype of, in the present case, a pumpkin plant, or a cell or tissue of that plant. A genetic complement thus represents the genetic makeup of a cell, tissue or plant, and a hybrid genetic complement represents the genetic make up of a hybrid cell, tissue or plant. The invention thus provides pumpkin plant cells that have a genetic complement in accordance with the pumpkin plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line HWN 130-1018T could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by pumpkin plant cells, tissues, plants, and seeds, formed by the combination of a haploid genetic complement of a pumpkin plant of the invention with a haploid genetic complement of a second pumpkin plant, preferably, another, distinct pumpkin plant. In another aspect, the present invention provides a pumpkin plant regenerated from a tissue culture that comprises a hybrid genetic complement of this invention.

In still yet another aspect, the invention provides a plant of an inbred pumpkin line that exhibits a combination of traits comprising resistance to Zucchini Yellow Mosaic Virus (ZYMV), Watermelon Mosaic Virus (WMV), and/or Cucumber Mosaic Virus. In certain embodiments, the combination of traits may be defined as controlled by genetic means for the expression of the combination of traits found in pumpkin line HWN 130-1018T.

In still yet another aspect, the invention provides a method of determining the genotype of a plant of pumpkin line HWN 130-1018T comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of pumpkin line HWN 130-1018T. This line shows uniformity and stability within the limits of environmental influence for the traits described hereinafter. Pumpkin line HWN 130-1018T provides sufficient seed yield. By crossing with a distinct and homozygous second plant, uniform F1 hybrid progeny can be obtained.

Line HWN 130-1018T exhibits a number of improved traits including resistance to Zucchini Yellow Mosaic Virus (ZYMV), Watermelon Mosaic Virus (WMV), and Cucumber Mosaic Virus. The development of the line can be summarized as follows.

A. Origin and Breeding History of Pumpkin Line HWN 130-1018T

HWN 130-1018T was derived from a cross between the Seminis proprietary breeding lines P56-ZWC and P44. P56-ZWC was itself derived from a cross between two earlier proprietary breeding lines, known as P21-ZWC and P8. P21-ZWC was in turn derived from a cross between Wizard (a proprietary hybrid once sold by Harris Moran seed company, now defunct) and the Seminis proprietary breeding line TS930097 (early generation source of the CZW3 transgene), as in the schematic below:

Wizard X TS930097 (donor of ZWC allele)→P21-ZWC (F4 generation Halloween type breeding line, plants with highly restricted vines, slightly elongated/pear-shaped fruits, and the precocious yellow character)

P21-ZWC X P8 (proprietary Halloween type breeding line, plants with spherical orange mature fruits and a vine type growth habit)→P56-ZWC P56-ZWC (F5 generation Seminis proprietary Halloween type breeding line, plants with bush type growth habit, early maturity, and a long, medium-thick peduncle) X P44 (Advanced generation Seminis proprietary breeding line purchased from Seneca Vegetable Seeds, plants with a vigorous semi-bush type growth habit and somewhat elongated blocky fruits with dark orange mature color, dark green peduncles, and light ribbing)→HWN 130-1018T.

The F1 generation of P56-ZWC X P44 was originally created in 1998 in Tifton, Ga. This hybrid was evaluated for horticultural characteristics including fruit type in the summer of 1999 in Georgia, where it was self pollinated to produce F2 seed. The F2 generation was again grown in Georgia in 2000, where seedlings were mechanically inoculated with ZYMV, and 13 individual plants were selected and self pollinated. Eight selections were harvested with good quality seed. The F3 generation was greenhouse grown in California in May of 2001, where it was manually inoculated with various pathogens, including ZYMV, and survivors were transplanted to the open field. Only families with uniformly resistant survivors without symptoms were selected and self pollinated, so that all subsequent generations were known to be homozygous for the CZW-3 transgene. Three selections were made in the F3 generation. The F4 generation was grown in the fall of 2001 in Florida, where 2 selections were made following self pollination.

Beginning in the F5 generation, evaluation of these breeding lines was based on both performance of the breeding lines and performance of hybrids created using these breeding lines. For the lineage that became HWN 130-1018T, the F5 generation was self pollinated during the 2002 early spring in a greenhouse concurrently with the production of 2 test hybrids, and 2 additional test hybrids were produced in the summer in a greenhouse in 2002. The F6 generation was greenhouse grown in the summer of 2003 in California, where it was both self pollinated and used in the production of hybrid seed to evaluate its use as a hybrid-parent line.

The F7 generation was grown in Florida in the fall of 2003, where it was self pollinated. The F8 generation was greenhouse grown in California in the early spring of 2004, where 26 plants were self pollinated in order to amplify the source of seed for the line HWN 130-1018T. These additional generations further establish uniformity of the parental line, and the initial stock needed to found the population of HWN 130-1018T based on a bulk of seed from 26 plants in the F8 generation all from the same F7 generation source. The pedigree and lineage of the F8 generation bulk is (P56-ZWC/P44)-3-2-2-2-3-4-3-M.

Since 2002, 19 unique Halloween type hybrids have been produced and evaluated which use HWN 130-1018T as a parent line. Hybrids derived from HWN 130-1018T have been observed in at least 10 states, including California, Florida, Texas, Idaho, Oregon, New York, Ohio, New Jersey, Pennsylvania, and Wisconsin. Hybrids derived from HWN 130-1018T produce semi-bush type plants with flat-round to deep-round shapes, dark orange mature fruit color, dark green peduncles, and medium sized fruit. Hybrids derived from HWN 130-1018T show high levels of resistance to one or more strains of Cucumber Mosaic Virus (CMV), Watermelon Mosaic Virus (WMV), and Zucchini Yellow Mosaic Virus (ZYMV). HWN 130-1018T has a complement of resistance traits and horticultural characteristics that make it ideal for many purposes, including for production of Halloween type pumpkin hybrids adapted to the United States, especially the areas where high density production of medium sized fruit is valuable. HWN 130-1018T may be used in the development of hybrids for other markets.

B. Physiological and Morphological Characteristics of Pumpkin Line HWN 130-1018T In accordance with one aspect of the present invention, there is provided a plant having the physiological and morphological characteristics of pumpkin line HWN 130-1018T. A description of the physiological and morphological characteristics of pumpkin line HWN 130-1018T is presented in Table 1.

TABLE 1

Physiological and Morphological Characteristics of Line HWN 130-1018T

| CHARACTERISTIC | HWN 130-1018T |
|---|---|
| 1. General Descriptors | |
| Fruit Shape/Variety Group | Pumpkin |
| Expected Primary Usage | Ornamental |
| Parts of Plant Providing Expected Primary Usage | Mature Fruit |
| Cotyledons Measured Between Full Expansion of $1^{st}$ and $2^{nd}$ True Leaves | Length to Width ratio - 1.82 Apex - Not Notched Veining - Obvious |
| 2. Main Stem | |
| Main Color | Dark Green (Nearly Entire Length - Multipik, Jack O'Lantern, Howden) |
| White Marks at Nodes | Present |
| Yellow Marks (Associated with Precocious Yellow Gene Complex) | Absent |
| Growth Habit (20 True Leaves) | |
| Bush | Semi-Bush (Taybelle, Table Ace, Jackpot) |
| Tendrils (20 True Leaves) | Absent or Rudimentary |
| Main Stem Internode Dimensions Observed after $20^{th}$ Internode Developed | |
| Length | Increases from $5^{th}$ to $15^{th}$ Internode |
| Width | Decreases from $5^{th}$ to $15^{th}$ Internode |
| 3. Petioles | |
| Derived from Main Stem Observed after $20^{th}$ Node Developed | |
| Length to Width Medial Ratio of 10th | 23.74 |
| Length to Width Medial Ratio of $15^{th}$ Petiole | 20.44 |
| Spininess (Prickles) Observed after $20^{th}$ Internode | Noticeably Spiny (Early Prolific Straightneck) |
| Angle of $6^{th}$ through $15^{th}$ on Main Stem | Horizontal (Caserta, less than $10°$) |
| 4. Laminae | |
| Lobing of $10^{th}$ and $15^{th}$ on Main Stem | Deeply Lobed |
| Dimensions of Leaf after $20^{th}$ Internode | 0.80 Length to Maximal Width Ratio of $10^{th}$ True Leaf |
| Dimensions of Leaf after $20^{th}$ Internode | 0.90 Length to Maximal Width ratio of $15^{th}$ True Leaf |
| Silver Blotching or Mottling | Silver Blotching Absent (Costata Romanesca, Early Prolific Straightnect) |

TABLE 1-continued

Physiological and Morphological Characteristics of Line HWN 130-1018T

| CHARACTERISTIC | HWN 130-1018T |
|---|---|
| 5. Flowers | |
| Number per Node Staminate on day of Anthesis on Main Stem (Between Nodes 11/20) | One (almost always) (Multipik, Cocozelle) |
| Length from Base of Calyx to Tip of Corolla | 111.2 mm |
| Exterior Width at Top of Calyx Cup | 19.2 mm |
| Pedicel Length | 177.7 mm |
| Length of Anther Column | 14.2 mm |
| Dominant Color of Corolla of Staminate Flower | Orange-yellow (Day of Anthesis) |
| Ring at Base of Interior of Staminate Corolla | Absent |
| Ring at Base of Interior of Pistillate Corolla | Yellow |
| Pistillate Flower on Day of Anthesis | |
| Length from Base of Calyx to Tip of Corolla | 95.4 mm |
| Pedicel Length | 68.0 mm |
| Ovary Color (Day Prior to Anthesis) | Green (Black Beauty, Multipik, Cocozelle, Clarita) |
| 6. Immature Fruit Size (3-5 Days Past Anthesis) | |
| Length (through Axis) to Medial Width Ratio | 1.20 |
| Length (through Axis) to Maximal Width Ratio | 1.03 |
| Color (3-5 Days Past Anthesis) | Light Green (Arlika, Clarita, Small Sugar, Ronde de Nice) |
| Fruit Flecks | Small (Nero di Milano, Raven, Magic Lantern) |
| Fruit Warting | Absent (Cocozelle, Multipik, Ronde de Nice, Gentry) |
| 6. Mature Fruit | |
| Surface Topograph | Grooving - Not so Distinct (Winter Luxury) |
| Dimensions (40 days past Anthesis) | 0.8 - Length (through Axis) to Maximal Width Ratio |
| Warting | Absent (Cocozelle, Multipik, Ronde de Nice) |
| Rind | Not Lignified (when Cutting Mature Fruit, Slice Smoothly and Easily) |
| Stylar End | Depressed (Howden) |
| Peduncle End | Depressed |
| Surface | Neither Netted or Cracked |
| Exterior Color | Intense Orange (Jack O'Lantern, Howden) |
| 7. Seed | |
| Hull (Mature) | Present with Normal Appearance |

*These are typical values. Values may vary due to environment. Other values that are substantially equivalent are within the scope of the invention.

Line HWN 130-1018T has been self-pollinated and planted for a number of generations to produce the homozygosity and phenotypic stability to make this line useful in commercial seed production. No variant traits have been observed or are expected for this line.

Pumpkin line HWN 130-1018T, being substantially homozygous, can be reproduced by planting seeds of the line, growing the resulting pumpkin plant under self-pollinating or sib-pollinating conditions and harvesting the resulting seeds using techniques familiar to one of skill in the art.

C. Breeding Pumpkin Line HWN 130-1018T

One aspect of the current invention concerns methods for crossing the pumpkin line HWN 130-1018T with itself or a second plant and the seeds and plants produced by such methods. These methods can be used for propagation of line HWN 130-1018T, or can be used to produce hybrid pumpkin seeds and the plants grown therefrom. Hybrid seeds are produced by crossing line HWN 130-1018T with second pumpkin parent line.

The development of new varieties using one or more starting varieties is well known in the art. In accordance with the invention, novel varieties may be created by crossing line HWN 130-1018T followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line HWN 130-1018T and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with HWN 130-1018T for the purpose of developing novel pumpkin lines, it will typically be preferred to choose those plants which either themselves exhibit one or more selected desirable characteristics or which exhibit the desired characteristic(s) when in hybrid combination. Examples of desirable traits of pumpkins include: high seed yield, high seed germination, seedling vigor, early fruit maturity, high fruit yield, ease of fruit setting, disease tolerance or resistance, and adaptability for soil and climate conditions. Consumer-driven traits, such as a preference for a given fruit size, shape, color, texture, and taste, are other traits that may be incorporated into new lines of pumpkin plants developed by this invention.

Particularly desirable traits that may be incorporated by this invention is improved resistance to different viral, fungal, and bacterial pathogens. Powdery mildew and Phytophthora blight are fungal diseases affecting various species of pumpkin. Fruit and leaf lesions and fruit rot are the commercially important aspects of these diseases. Bacterial leaf spot and bacterial wilt are other diseases affecting pumpkin plants, especially during a wet season. Viral pathogens affecting pumpkin plants include the Cucurbit Leaf Crumple Virus and the Papaya Ringspot Virus.

Improved resistance to insect pests is another desirable trait that may be incorporated into new lines of pumpkin plants developed by this invention. Insect pests affecting the various species of pumpkin include the Striped cucumber beetle, the Squash bug, aphids, and mites.

D. Performance Characteristics

As described above, line HWN 130-1018T exhibits desirable agronomic traits, including resistance to ZYMV, WMV, and CMV. In addition, hybrids made using HWN 130-1018T as a parent line also demonstrate multivirus resistance, along with other desirable horticultural traits. Hybrids made with the line were the subject of objective analysis of performance traits of hybrids made using HWN 130-1018T compared to other Seminis Halloween type pumpkin products. The results of the analysis are presented below in Table 2. During the year and at the location where this analysis was performed, natural incidence of viral diseases was unusually low, so that resistance levels for ZYMV, WMV, and CMV were not observable in this trial. As the truly unique and valuable feature of hybrids derived from HWN 130-1018T is their multivirus resistance, the horticultural characteristics of these lines need only match those of a typical commercial product to demonstrate value to the farmer.

TABLE 2

Horticultural Scoring Of Halloween Type Pumpkin Variety From Seminis Using HWN 130-1018T Compared To Those Not Produced Using HWN 130-1018T

| Cultivar | HWN 130-1018T Hybrid | DTM | Fruit color | Handle color | Handle length | Handle width | Fruit Uniformity | Plant Habit | Avg Fruit wt |
|---|---|---|---|---|---|---|---|---|---|
| PXT 13024949 III | Yes | 69 | 3 | 5 | 5 | 5 | 3 | 3 | 15.7 |
| PXT 13035718 III | No | 78 | 7 | 6 | 4 | 6 | 2 | 2 | 14.0 |
| APPALACIAN | No | 79 | 5 | 6 | 7 | 6 | 5 | 5 | 22.4 |
| HARVESTMOON | No | 75 | 7 | 7 | 6 | 7 | 3 | 3 | 8.8 |
| Longface | No | 76 | 5 | 4 | 5 | 7 | 5 | 5 | 18.1 |
| Orange Smoothie | No | 75 | 5 | 5 | 7 | 7 | 3 | 1 | 5.7 |
| PHANTOM | No | 85 | 6 | 6 | 6 | 4 | 5 | 5 | 14.8 |
| PS159011 | No | 87 | 6 | 5 | 7 | 7 | 4 | 3 | 1.5 |
| PX 13056567 | No | 78 | 2 | 4 | 5 | 5 | 5 | 5 | 23.5 |
| Schooltime | No | 75 | 6 | 4 | 7 | 7 | 3 | 1 | 8.1 |
| Spirit | No | 73 | 8 | 5 | 6 | 7 | 3 | 2 | 12.6 |
| Spooktacular | No | 75 | 7 | 7 | 5 | 6 | 2 | 5 | 3.4 |
| Trickster | No | 75 | 5 | 6 | 3 | 5 | 7 | 5 | 2.2 |

Cultivar describes the commercial or pre-commercial name of the hybrid being evaluated. HWN 130-1018T Hybrid describes whether the cultivar being evaluated uses the parent in question in production of the hybrid. Remaining traits are rated on a 1 to 9 scale, with 1 being ideal and 9 being completely unacceptable. DTM describes the approximate number of days from sowing to harvest maturity in the trial where these cultivars were evaluated. Fruit color describes the intensity of orange color development on the mature fruit in the plot, where 1 represents uniformly deep orange fruits and 9 represents very poorly colored and/or non-uniformly colored fruits. Handle color describes the color intensity and uniformity on the peduncle (fruit stem) of the mature fruits, where 1 represents an even and very dark green (near black) peduncle and 9 represents a white or lightly colored and mottled peduncle. Handle length describes the length of the peduncle on the mature fruit, where 1 is averaging approximately 1 inch or less and 9 is averaging approximately 9 inches or more. Handle width describes the peduncle in cross section relative to fruit size, where 1 represents a peduncle that is exceptionally wide, such as a 3 inch wide peduncle on an 18 pound fruit, and 9 represents an unacceptably narrow peduncle, such as a ½ inch wide peduncle on an 18 pound fruit. Fruit uniformity describes the overall level of variation for mature fruit size, shape, color, and weight. Plant Habit describes the space required for each plant, where 1 represents a near bush type growth habit and 9 represents an extremely vigorous vining growth habit. Fruit weight is the average weight of the 10 fruits harvested nearest the center of each plot, measured in pounds. As shown above, the hybrid using HWN 130-1018T as a parent exhibit improved earliness, fruit color, fruit uniformity, and growth habit when compared to most other Seminis commercial and pre-commercial Halloween type pumpkin products. One important aspect of the invention thus provides seed of the variety for commercial use. Such seed can be reproduced by crossing the line under self- or sib-pollinating conditions.

E. Further Embodiments of the Invention

When the term pumpkin line HWN 130-1018T is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those pumpkin plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental pumpkin plant which contributes the locus for the desired characteristic is termed the nonrecurrent or donor parent. This terminology refers to the fact that the nonrecurrent parent is used one time in the backcross protocol and therefore does not recur. The parental pumpkin plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a pumpkin plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny pumpkin plants of a backcross in which HWN 130-1018T is the recurrent parent comprise (i) the desired trait from the non-recurrent parent and (ii) all of the physiological and morphological characteristics of pumpkin line HWN 130-1018T as determined at the 5% significance level when grown in the same environmental conditions.

Pumpkin varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the downy mildew resistance trait. For this selection process, the progeny of the initial cross are sprayed with downy mildew spores prior to the backcrossing. The spraying eliminates any plants which do not have the desired downy mildew resistance characteristic, and only those plants which have the downy mildew resistance gene are used in the subsequent backcross. This process is then repeated for all additional backcross generations.

Selection of pumpkin plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of pumpkin are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived from Pumpkin Line HWN 130-1018T by Genetic Engineering

Many useful traits that can be introduced by backcrossing, as well as directly into a plant, are those which are introduced by genetic transformation techniques. Genetic transformation may therefore be used to insert a selected transgene into the pumpkin line of the invention or may, alternatively, be used for the preparation of transgenes which can be introduced by backcrossing. Methods for the transformation of plants, including pumpkin plants, are well known to those of skill in the art (see, e.g., Schroeder et al., 1993). Techniques which may be employed for the genetic transformation of pumpkin plants include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

*Agrobacterium*-mediated transformation of pumpkin explant material and regeneration of whole transformed pumpkin plants (including tetraploids) from the transformed shoots has been shown to be an efficient transformation method (U.S. Pat. No. 5,262,316).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target pumpkin cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pumpkin plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the pumpkin lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a pumpkin plant according to the invention. Non-limiting examples of particular genes and corresponding phenotypes one may choose to introduce into a pumpkin plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a pumpkin variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a pumpkin plant by transformation.

H. Deposit Information

A deposit of pumpkin line HWN 130-1018T, disclosed above and recited in the claims, has been made with the American Type Culture Collection (ATCC), 10801 University Blvd., Manassas, Va. 20110-2209. The date of deposit was Apr. 30, 2007. The accession number for those deposited seeds of pumpkin line HWN 130-1018T is ATCC Accession No. PTA-8392. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:
U.S. Pat. No. 5,262,316
U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 7,087,819
An et al., *Plant Physiol.*, 88:547, 1988.
Berke, J. *New Seeds*, 1:3-4, 1999.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Chae et al., *Capsicum Eggplant Newsltr.*, 22:121-124, 2003.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125,1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Midwest Veg. Prod. Guide for Commercial Growers (ID:56), 2003
Odel et al., *Nature*, 313:810, 1985.
Omirulleh et al., *Plant Mol. Biol.*, 21(3):415-428, 1993.
Pandal et al., *Theor. Appl. Gene.*, 68(6):567-577, 1984.
Pickersgill and Barbara, *Euphytica*, 96(1):129-133, 1997
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248

What is claimed is:

1. A seed of pumpkin line HWN 130-1018T, a sample of seed of said line having been deposited under ATCC Accession Number PTA-8392.

2. A plant grown from the seed of claim 1.

3. A plant part of the plant of claim 2.

4. The plant part of claim 3, wherein said part is selected from the group consisting of a fruit, pollen, rootstock, scion, an ovule and a cell.

5. A pumpkin plant, or a part thereof, having all the physiological and morphological characteristics of the pumpkin plant of claim 2.

6. A tissue culture of regenerable cells of pumpkin line HWN 130-1018T, a sample of seed of said line having been deposited under ATCC Accession Number PTA-8392.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A pumpkin plant regenerated from the tissue culture of claim 6, wherein the regenerated plant expresses all of the physiological and morphological characteristics of pumpkin line HWN 130-1018T, a sample of seed of said line having been deposited under ATCC Accession Number PTA-8392.

9. A method of producing pumpkin seed, said method comprising crossing the plant of claim 2 with itself or a second pumpkin plant.

10. The method of claim 9, wherein the plant of pumpkin line HWN 130-1018T is the female parent.

11. An F1 hybrid seed produced by the method of claim 9.

12. An F1 hybrid plant produced by growing the seed of claim 11.

13. A method for producing a seed of a line HWN 130-1018T-derived pumpkin plant said method comprising the steps of:
    (a) crossing a pumpkin plant of line HWN 130-1018T, a sample of seed of said line having been deposited under ATCC Accession Number PTA-8392, with a second pumpkin plant; and
    (b) allowing seed of a HWN 130-1018T-derived pumpkin plant to form.

14. The method of claim 13, further comprising the steps of:
    (c) crossing a plant grown from said HWN 130-1018T-derived pumpkin seed with itself or a second pumpkin plant to yield additional HWN 130-1018T-derived pumpkin seed;
    (d) growing said additional HWN 130-1018T-derived pumpkin seed of step (c) to yield additional HWN 130-1018T-derived pumpkin plants; and
    (e) repeating the crossing and growing steps of (c) and (d) to generate further HWN 130-1018T-derived pumpkin plants.

15. A method of vegetatively propagating a plant of pumpkin line HWN 130-1018T said method comprising the steps of:
    (a) collecting tissue capable of being propagated from a plant of pumpkin line HWN 130-1018T, a sample of seed of said line having been deposited under ATCC Accession Number PTA-8392;
    (b) cultivating said tissue to obtain proliferated shoots; and
    (c) rooting said proliferated shoots to obtain rooted plantlets.

16. The method of claim 15, further comprising growing plants from said rooted plantlets.

17. A method of introducing a desired trait into pumpkin line HWN 130-1018T said method comprising:
    (a) crossing a plant of line HWN 130-1018T, a sample of seed of said line having been deposited under ATCC Accession Number PTA-8392, with a second pumpkin plant that comprises a desired trait to produce F1 progeny;

(b) selecting an F1 progeny that comprises the desired trait;
(c) crossing the selected F1 progeny with a plant of line HWN 130-1018T, a sample of seed of said line having been deposited under ATCC Accession Number PTA-8392, to produce backcross progeny;
(d) selecting backcross progeny comprising the desired trait and the physiological and morphological characteristic of pumpkin line HWN 130-1018T; and
(e) repeating steps (c) and (d) three or more times in succession to produce selected fourth or higher backcross progeny that comprise the desired trait.

18. A pumpkin plant produced by the method of claim 17.

19. A method of producing a plant of pumpkin line HWN 130-1018T, a sample of seed of said line having been deposited under ATCC Accession Number PTA-8392, comprising an added desired trait, the method comprising introducing a transgene conferring the desired trait into a plant of pumpkin line HWN 130-1018T.

20. A plant that comprises all of the physiological and morphological characteristics of pumpkin line HWN 130-1018T, a sample of seed of said line having been deposited under ATCC Accession Number PTA-8392.

21. A seed that produces the plant of claim 20.

22. A method of determining the genotype of the plant of claim 2, said method comprising obtaining a sample of nucleic acids from said plant and detecting in said nucleic acids a plurality of polymorphisms.

23. The method of claim 22, further comprising the step of storing the results of the step of detecting the plurality of polymorphisms on a computer readable medium.

24. A method of producing pumpkins said method comprising:
(a) obtaining the plant of claim 2, wherein the plant has been cultivated to maturity; and
(b) collecting pumpkins from the plant.

* * * * *